(12) United States Patent
Wells et al.

(10) Patent No.: US 9,733,164 B2
(45) Date of Patent: Aug. 15, 2017

(54) LAMELLA CREATION METHOD AND DEVICE USING FIXED-ANGLE BEAM AND ROTATING SAMPLE STAGE

(75) Inventors: Andrew B. Wells, Portland, OR (US); N. William Parker, Hillsboro, OR (US); Clive D. Chandler, Portland, OR (US); Mark W. Utlaut, Scappoose, OR (US)

(73) Assignee: FEI Company, Hillsboro, OR (US)

( * ) Notice: Subject to any disclaimer, the term of this patent is extended or adjusted under 35 U.S.C. 154(b) by 533 days.

(21) Appl. No.: 13/493,735

(22) Filed: Jun. 11, 2012

(65) Prior Publication Data

US 2013/0328246 A1 Dec. 12, 2013

(51) Int. Cl.
*H01J 37/26* (2006.01)
*H01J 37/20* (2006.01)
*G01N 1/32* (2006.01)
*H01J 37/302* (2006.01)
*H01J 37/305* (2006.01)

(52) U.S. Cl.
CPC ............ *G01N 1/32* (2013.01); *H01J 37/3023* (2013.01); *H01J 37/3056* (2013.01); *H01J 2237/31745* (2013.01)

(58) Field of Classification Search
CPC .............. G01N 1/32; H01J 2237/31745; H01J 37/3023; H01J 37/3056
USPC ............. 264/400, 406, 482, 485; 250/440.11
See application file for complete search history.

(56) References Cited

U.S. PATENT DOCUMENTS

| 6,039,000 | A  | 3/2000  | Libby et al.     |
|-----------|----|---------|------------------|
| 6,664,552 | B2 | 12/2003 | Shichi et al.    |
| 6,900,447 | B2 | 5/2005  | Gerlach et al.   |
| 7,009,187 | B2 | 3/2006  | Gerlach et al.   |
| 8,076,650 | B2 | 12/2011 | Smith et al.     |
| 8,168,961 | B2 | 5/2012  | Straw et al.     |
| 8,278,220 | B2 | 10/2012 | Holtermann et al.|
| 8,283,629 | B1 | 10/2012 | Tuggle et al.    |
| 8,314,410 | B2 | 11/2012 | Straw et al.     |
| 8,405,054 | B2 | 3/2013  | Smith et al.     |

(Continued)

FOREIGN PATENT DOCUMENTS

| EP | 1209737 | 5/2002 |
|----|---------|--------|
| EP | 1447656 | 8/2004 |

(Continued)

*Primary Examiner* — Robert J Grun
(74) *Attorney, Agent, or Firm* — Scheinberg & Associates, P.C.; John B. Kelly; John E. Hillert

(57) ABSTRACT

A system for creating a substantially planar face in a substrate, the system including directing one or more beams at a first surface of a substrate to remove material from a first location, the beam being offset from a normal to the first surface by a curtaining angle; sweeping the one or more beams in a plane that is perpendicular to the first surface to mill one or more initial cuts, the initial cuts exposing a second surface that is substantially perpendicular to the first surface; rotating the substrate about an axis other than an axis normal to the first beam or parallel to the first beam; directing the first beam at the second surface to remove additional material from the substrate without changing the curtaining angle; and scanning the one or more beams in across the second surface to mill one or more finishing cuts.

18 Claims, 17 Drawing Sheets

(56) References Cited

U.S. PATENT DOCUMENTS

| | | | |
|---|---|---|---|
| 2002/0170675 A1* | 11/2002 | Libby | H01J 37/3056 |
| | | | 156/345.39 |
| 2004/0151991 A1 | 8/2004 | Stewart et al. | |
| 2008/0073586 A1* | 3/2008 | Iwasaki | 250/492.21 |
| 2008/0142735 A1 | 6/2008 | Chandler et al. | |
| 2011/0115129 A1 | 5/2011 | Straw et al. | |
| 2011/0163068 A1 | 7/2011 | Utlaut et al. | |
| 2011/0226947 A1 | 9/2011 | Takahashi et al. | |
| 2012/0103945 A1 | 5/2012 | Straw et al. | |
| 2012/0200007 A1 | 8/2012 | Straw et al. | |
| 2013/0248354 A1 | 9/2013 | Keady et al. | |

FOREIGN PATENT DOCUMENTS

| | | |
|---|---|---|
| EP | 1643232 | 4/2006 |
| EP | 2009421 | 12/2008 |
| EP | 2590203 | 5/2013 |

\* cited by examiner

LAMELLA CREATION METHOD AND DEVICE USING FIXED-ANGLE BEAM AND ROTATING SAMPLE STAGE

TECHNICAL FIELD OF THE INVENTION

The present invention relates to preparation of samples and methods of sample handling for analysis by electron microscopes.

BACKGROUND OF THE INVENTION

Semiconductor manufacturing, such as the fabrication of integrated circuits, typically entails the use of photolithography. A semiconductor substrate on which circuits are being formed, usually a silicon wafer, is coated with a material, such as a photoresist, that changes solubility when exposed to radiation. A lithography tool, such as a mask or reticle, positioned between the radiation source and the semiconductor substrate casts a shadow to control which areas of the substrate are exposed to the radiation. After the exposure, the photoresist is removed from either the exposed or the unexposed areas, leaving a patterned layer of photoresist on the wafer that protects parts of the wafer during a subsequent etching or diffusion process.

The photolithography process allows multiple integrated circuit devices or electromechanical devices, often referred to as "chips," to be formed on each wafer. The wafer is then cut up into individual dies, each including a single integrated circuit device or electromechanical device. Ultimately, these dies are subjected to additional operations and packaged into individual integrated circuit chips or electromechanical devices.

During the manufacturing process, variations in exposure and focus require that the patterns developed by lithographic processes be continually monitored or measured to determine if the dimensions of the patterns are within acceptable ranges. The importance of such monitoring, often referred to as process control, increases considerably as pattern sizes become smaller, especially as minimum feature sizes approach the limits of resolution available by the lithographic process. In order to achieve ever-higher device density, smaller and smaller feature sizes are required. This may include the width and spacing of interconnecting metallization lines, spacing and diameter of contact holes and vias, and the surface geometry such as corners and edges of various features. Features on the wafer are three-dimensional structures and a complete characterization must describe not just a surface dimension, such as the top width of a line or trench, but a complete three-dimensional profile of the feature. Process engineers must be able to accurately measure the critical dimensions (CD) of such surface features to fine tune the fabrication process and assure a desired device geometry is obtained.

Typically, CD measurements are made using instruments such as a scanning electron microscope (SEM). In a scanning electron microscope (SEM), a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features continue to get smaller and smaller, however, there comes a point where the features to be measured are too small for the resolution provided by an ordinary SEM.

Transmission electron microscopes (TEMs) allow observers to see extremely small features, on the order of nanometers. In contrast to SEMs, which only image the surface of a material, TEM also allows analysis of the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite site. Samples are typically less than 100 nm thick.

In a scanning transmission electron microscope (STEM), a primary electron beam is focused to a fine spot, and the spot is scanned across the sample surface. Electrons that are transmitted through the substrate are collected by an electron detector on the far side of the sample, and the intensity of each point on the image corresponds to the number of electrons collected as the primary beam impacts a corresponding point on the surface.

As semiconductor geometries continue to shrink, manufacturers increasingly rely on transmission electron microscopes (TEMs) for monitoring the process, analyzing defects, and investigating interface layer morphology. The term "TEM" as used herein refers to a TEM or a STEM, and references to preparing a sample for a TEM are to be understood to also include preparing a sample for viewing on an STEM. Because a sample must be very thin for viewing with transmission electron microscopy (whether TEM or STEM), preparation of the sample can be delicate, time-consuming work.

Thin TEM samples cut from a bulk sample material are known as "lamellae". Lamellae are typically less than 100 nm thick, but for some applications a lamella must be considerably thinner. With advanced semiconductor fabrication processes at 30 nm and below, a lamella needs to be less than 20 nm in thickness in order to avoid overlap among small scale structures. Currently, thinning below 30 nm is difficult and not robust. Thickness variations in the sample result in lamella bending, overmilling, or other catastrophic defects. For such thin samples, lamella preparation is a critical step in TEM analysis that significantly determines the quality of structural characterization and analysis of the smallest and most critical structures.

Even though the information that can be discovered by TEM analysis can be very valuable, the entire process of creating and measuring TEM samples has historically been so labor intensive and time consuming that it has not been practical to use this type of analysis for manufacturing process control. The use of focused ion beam (FIB) systems to create lamellae for TEM microscopy is known in the art. FIB systems are capable of milling lamella sufficiently thin to be used in a TEM system. The use of dual-beam systems for TEM sample preparation is known in the art. A dual-beam system has a FIB column for milling a lamella from a bulk sample and a SEM column for imaging the lamella, typically as the lamella is being milled. Dual-beam systems improve the time required to prepare samples for TEM analysis. While the use of FIB methods in sample preparation has reduced the time required to prepare samples for TEM analysis down to only a few hours, it is not unusual to analyze 15 to 50 TEM samples from a given wafer. As a result, speed of sample preparation is a very important factor in the use of TEM analysis, especially for semiconductor process control.

FIG. 1A shows a prior art FIB system in an orientation for performing initial milling on a bulk sample material to create a sample lamella for TEM analysis. The bulk sample material, substrate 108, is loaded into sample stage 106 of the tool. Substrate 108 is oriented so that its top surface is perpendicular to focused ion beam 104 emitted from FIB column 102. Most of the ion beam machining done to create lamella 110 is performed with substrate 108 and FIB column 102 in this orientation. Due to the focusing (i.e., a convergent conical shape) and the path of ion beam 104, this perpendicular milling causes lamella 110 to be tapered from top to bottom. That is, lamella 110 is thinner at the top than it is at the bottom. Furthermore, lamella 110 remains securely attached to substrate 108 at boundary 114. Lamella 110 must be removed from substrate 108 before it can be used in the TEM. In addition, material removed from substrate 108 while milling with ion beam 104 in the vertical orientation may be redeposited on or flow onto the face of lamella 110, forming amorphous layer 112. Amorphous layer 112 reduces the quality of the TEM analysis and must be removed or polished away before lamella 110 can be used with the TEM.

FIG. 1B shows a prior art FIB system in a tilted orientation for post-processing a sample lamella using overtilting, polishing, and/or undercutting. Overtilting is the process of removing the taper from the sides of lamella 110 to make the faces of lamella 110 substantially parallel. Polishing is the process of removing amorphous layer(s) 112 from lamella 110 that collected on lamella 110 from the previous initial milling. Undercutting is the process of partially or fully detaching lamella 110 from substrate 108 at or near boundary 114. Prior art lamella-creation tools orient FIB column 102 so that ion beam 104 is in the vertical orientation during the initial machining of substrate 108 (i.e., normal to the top surface of substrate 108). After the initial machining of substrate 108, in order to perform the processes of overtilting, polishing, and undercutting, the sample must be tilted away from a position that is perpendicular to ion beam 104 in both directions so that the additional ion milling can be performed. Either sample stage 106 or FIB column 102 is rotated an angle 116 about the long axis of lamella 110. That is, either sample stage 106 or FIB column 102 is rotated an angle 116 relative to a plane defined by the long axis of lamella 110 and the normal to the top surface of substrate 108. Put another way, sample stage 106 or FIB column 102 is rotated about an axis that is perpendicular to the sheet of FIG. 1A and located within the cross-section of lamella 110 shown in FIG. 1A, preferably near the center of the cross-section of lamella 110.

In the architectures known in the prior art, either sample stage 106 or FIB column 102 must be tilted about an axis that is perpendicular to the plane defined by FIB column 102 and a normal to the top surface of substrate 108 after the initial milling to perform any required post-processing on lamella 110. The provision of either of these tilts (i.e., stage or column tilt) to the tool is complex and adds to the expense, maintenance, and fragility of the tool. In prior art systems, if FIB column 102 is held in a fixed position throughout the entire lamella preparation processes, then sample stage 106 must have five degrees of freedom: translation in the X, Y, and Z directions, rotation about the axis perpendicular to the top surface of the substrate, and rotation about the axis perpendicular to FIB column 102. Alternatively, if sample stage 106 is made to have only four degrees of freedom (X, Y, Z, and rotation about the axis perpendicular to the sample's top surface), then FIB column 102 must rotate with respect to the rest of the tool during milling to perform overfilling, polishing, and undercutting.

A TEM sample preparation system having a sample stage 106 and/or FIB column 102 that can be tilted accurately within an acceptable limits of drift (on the order of nanometers) is complex, expensive, and requires additional maintenance. A TEM sample preparation system having a sample stage 106 with only four degrees of freedom and a FIB column 102 that remains in a fixed position would, all other things being equal, cost less than the tools described above, be easier to assemble and maintain, and be less likely to break down. It is thus desirable to be able to perform angled milling with FIB column 102 without having to tilt the sample with respect to ion beam 104 during processing.

Additionally, lamellae formed using the prior art methods described above are subject to an undesirable side effect known as "curtaining." FIG. 2 shows a sample 200 exhibiting the curtaining effect. When substrate 108 is formed from a heterogeneous structure (e.g, metal gates and shields along with silicon and silicon dioxide), ion beam 104 differentially mills different elements at different mill rates. Some metal elements tend to shadow the lighter material underneath them. For example, sample 200 comprises silicon portion 202 and tungsten portion 204. Silicon portion 202 is milled at a higher reate than tungsten portion 204. The resulting effect is a rippled lamella face, or curtain 206, which is not milled back as far in the areas of metal as it is milled in the areas without metal. This effect is called "curtaining" because the rippled features on the lamella face resemble a hanging curtain. When the ion beam is directed vertically (i.e., perpendicular to the top surface of the substrate), the curtaining effect is most pronounced. Curtaining artifacts reduce the quality of the TEM imaging and limit the minimal useful specimen thickness. For ultra-thin TEM samples, the two cross-section faces are in very close proximity so thickness variations from curtaining effects can cause a sample lamella to be unusable. Thus, it is desirable to reduce curtaining artifacts during the preparation of TEM sample lamellae.

Although the foregoing description of the process for lamella preparation has been presented in the context of semiconductor fabrication, lamella preparation for other applications is also now a common practice. For example, in biological imaging, it is often advantageous to create lamellae from resin-embedded or cryogenically-frozen samples of cells or tissues. A TEM or STEM is then used to image these lamella, thereby gaining information about various cellular ultrastructures.

In addition, the micro- and nanomachining procedures described above in the context of lamella preparation may also be employed in other nanofabrication procedures such as MEMs fabrication and other processes for the creation of mechanical, electrical, and electromechanical devices, especially in cases where these structures span size ranges from tens of micrometers to nanometer sizes.

The beam positioning and tilting procedures described above in the context of focused ion beams may also have application for other types of microfabrication processes, for example, the use of waterjet cutters and laser beams.

SUMMARY OF THE INVENTION

An embodiment of the present invention includes a method for creating a substantially planar face in a substrate, the method including directing a first beam at a first surface of a substrate to remove material from a first location in the substrate, the first beam being offset from a normal to the first surface by a first nonzero curtaining angle; sweeping the first beam in a plane that is perpendicular to the first surface to mill one or more initial cuts in the substrate, the initial cuts exposing a second surface that is substantially perpendicular to the first surface; rotating the substrate through a nonzero rotation angle about an axis other than an axis that is normal to the first beam or parallel to the first beam; directing the first beam at the second surface to remove additional material from the substrate without changing the first nonzero curtaining angle; and scanning the first beam in a pattern across the second surface to mill one or more finishing cuts in the substrate.

Another embodiment of the present invention includes an apparatus for creating a substantially planar face in a substrate, the apparatus including a first particle source for emitting particles to mill features in a substrate; a first focusing column for forming the particles emitted from the first particle source into a first beam and directing the first beam to impinge upon the substrate; and a sample stage for holding the substrate in a fixed position relative to the sample stage, in which the sample stage can rotate about no more than one axis.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Embodiments of the present invention are directed to devices and methods for creating flat-sided cuts in a sample substrate to create sample lamellae, preferably for use in a transmission electron microscope (TEM). The embodiments include positioning an ion beam in such a way that the beam is not normal to the top surface of the sample substrate. The beam is scanned in the plane defined by the ion beam column and a normal to the top surface of substrate, and the substrate is rotated about the normal to its top surface in order to vary the apparent milling angle.

Figure 1A:
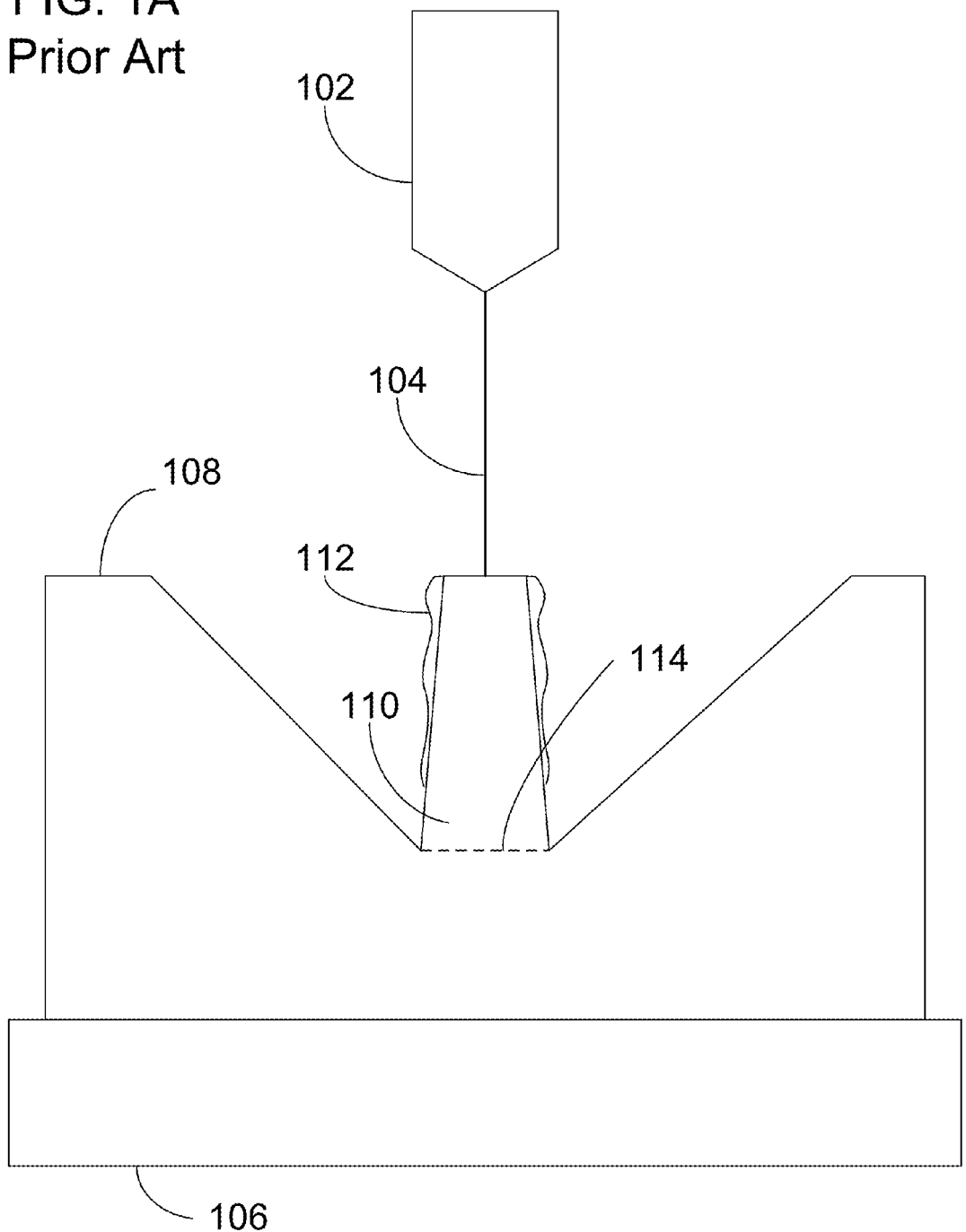
FIG. 1A shows a prior art FIB system in an initial orientation for preparing a sample lamella for TEM analysis from a substrate.
Figure 1B:
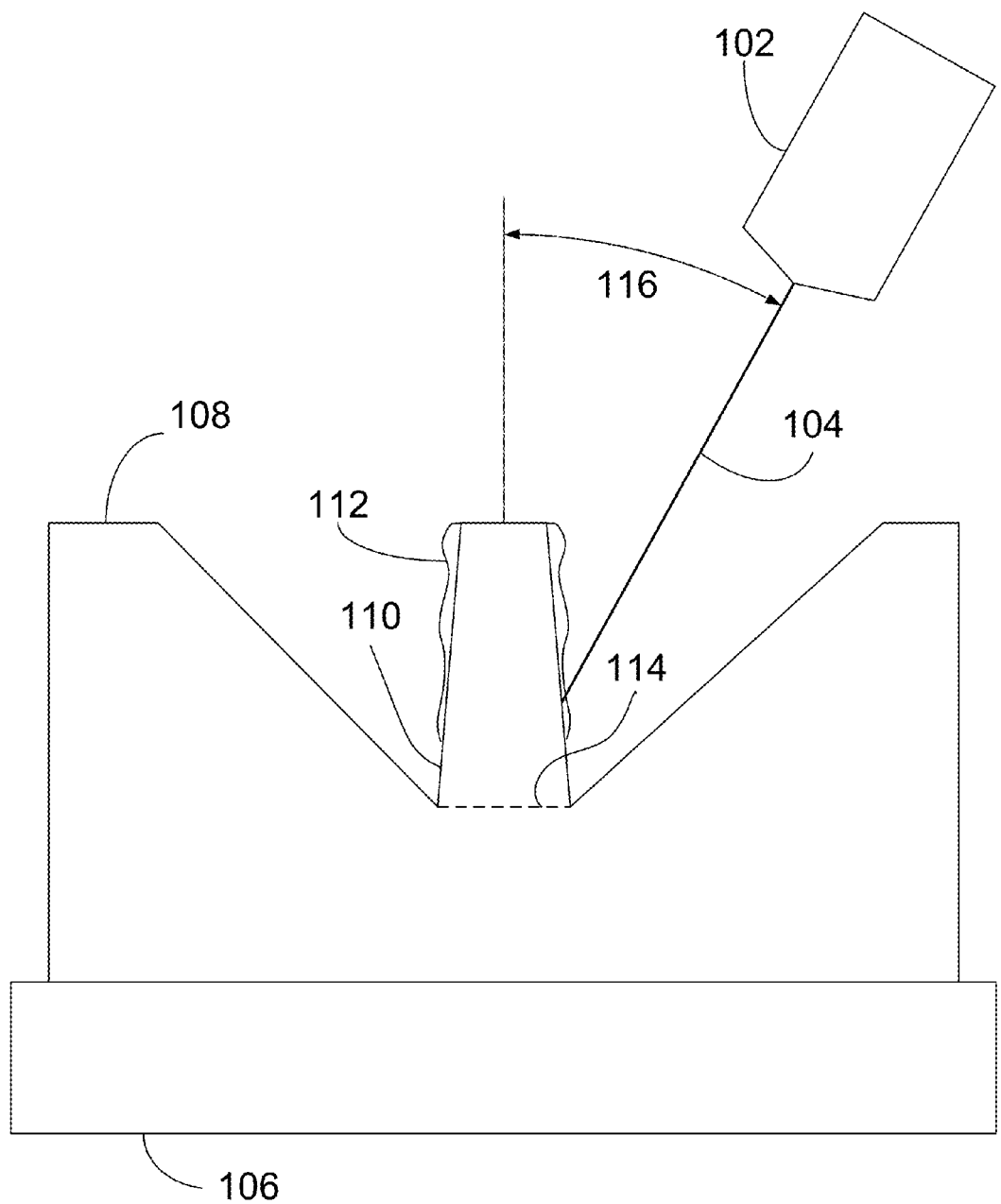
FIG. 1B shows a prior art FIB system in a tilted orientation for post-processing a sample lamella using overfilling, polishing, and/or undercutting.
Figure 2:
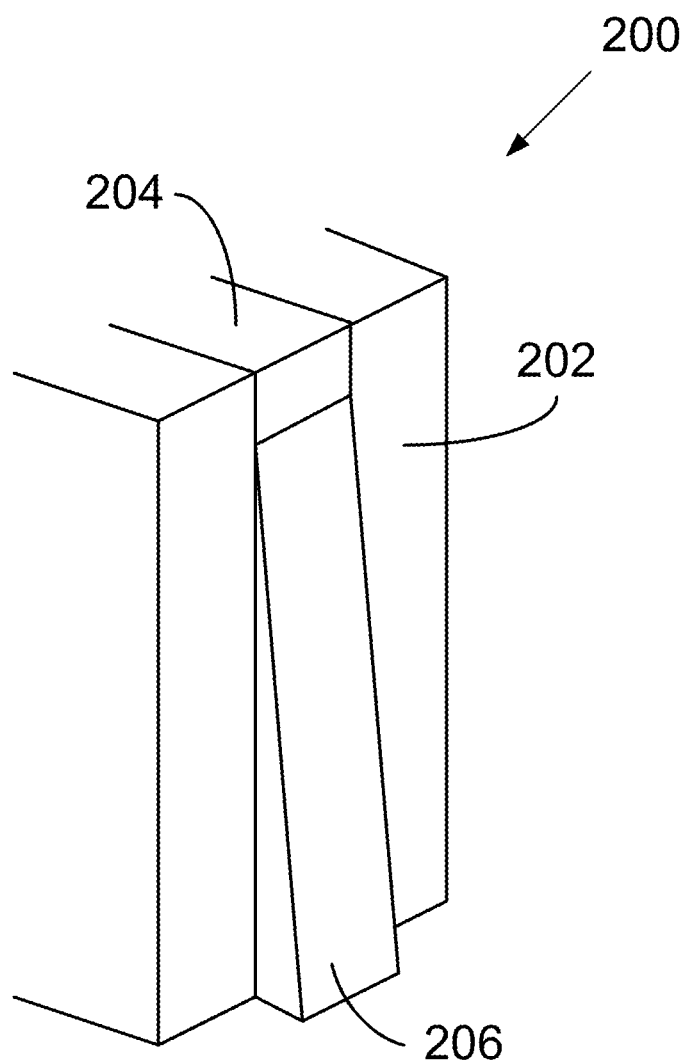
FIG. 2 shows a sample 200 exhibiting the curtaining effect.
Figure 3:
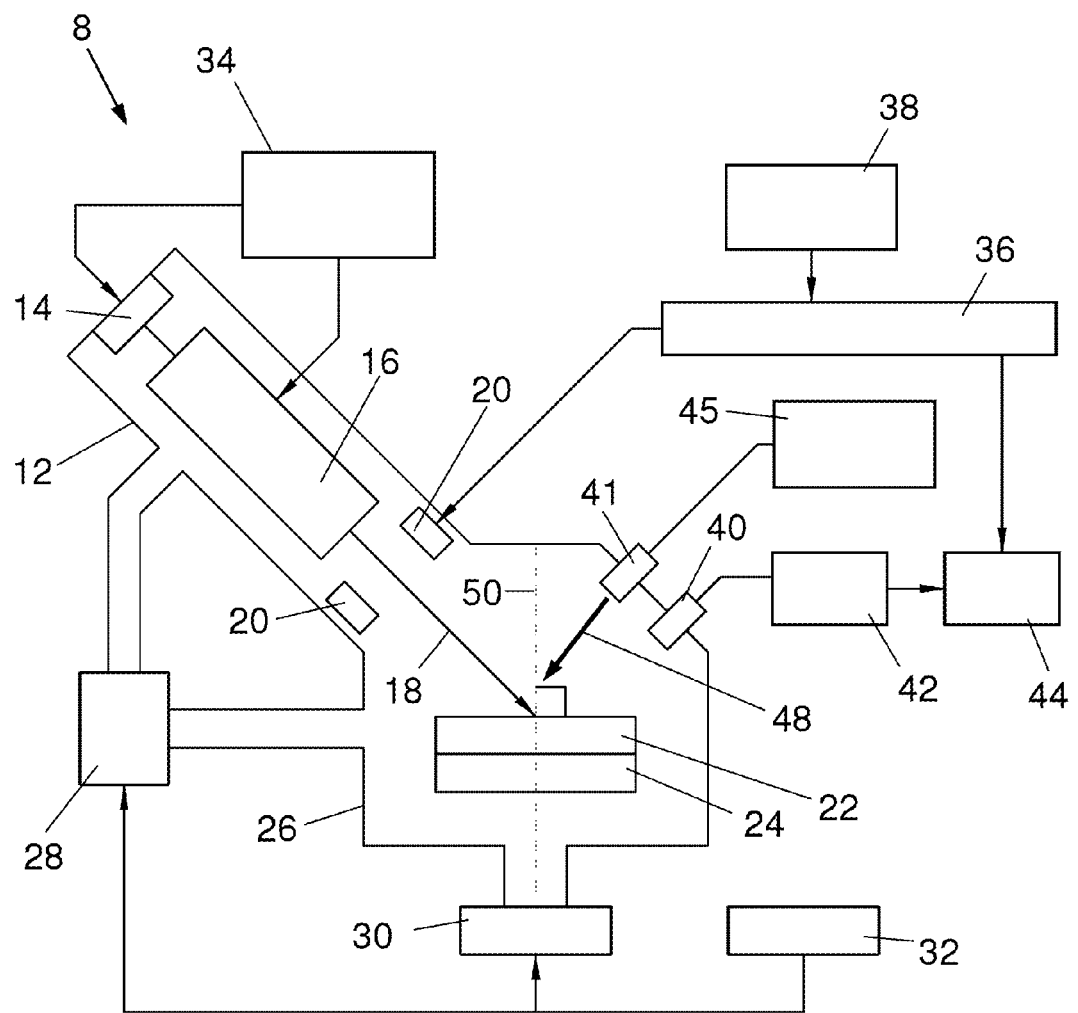
FIG. 3 shows a particle beam system used to implement one or more embodiments of the present invention.

FIG. 3 shows a focused ion beam system 8 that can be used to implement one or more embodiments of the present invention. Focused ion beam system 8 includes evacuated envelope 12 in which ion source 14 is located to provide ions for ion beam focusing column 16. Ion beam 18 passes from source 14 through column optics 16 and between electrostatic deflection mechanism 20 toward substrate 22, which comprises, for example, a semiconductor device positioned on sample stage 24 within lower chamber 26. In at least one embodiment, sample stage 24 has no more than four degrees of freedom, obviating the need for tilting stage. In alternative embodiments, sample stage 24 may include a tilting stage having more than four degrees of freedom. Preferably, sample stage 24 can translate in the x, y, and z directions, and sample stage 24 can rotate about single axis that is perpendicular to the top surface of sample stage 24.

High voltage power supply 34 is connected to ion source 14 as well as to appropriate electrodes in focusing column 16 for forming ion beam 18 and directing ion beam 18 toward sample 22. Deflection controller and amplifier 36, operated in accordance with a prescribed pattern provided by pattern generator 38, is coupled to deflection plates 20 whereby beam 18 may be controlled to trace out a corresponding pattern on a surface of sample 22 (also termed "substrate"). In some systems, the deflection plates 20 are placed before the final lens (i.e., within focusing column 16), as is well known in the art.

The ion beam source 14 is brought to a focus at substrate 22 for either modifying a surface of substrate 22 by ion milling, material deposition, or for the purpose of imaging the surface. A charged particle multiplier 40 used for detecting secondary ion or electron emission for imaging can be connected to video circuit and amplifier 42. Other image detectors known in the art can also be used, such as backscattered electron or x-ray detectors. Video circuit and amplifier 42 supplying a video signal for video monitor 44. Video monitor 44 also receives deflection signals from controller 36. The location of charged particle multiplier 40 within chamber 26 can vary in different embodiments. For example, in one embodiment, charged particle multiplier 40 can be coaxial with the ion beam and include a hole for allowing the ion beam to pass. A scanning electron microscope 41 (SEM), along with its power supply and controls 45, are preferably provided with the FIB system 8. SEM 41 can be used to image the substrate with electron beam 48 after milling with the FIB 18 or concurrently with FIB milling to monitor the progress of the milling process.

Signals applied to deflection controller and amplifier 36, cause the beam 18 to move within a target area to be imaged or milled on substrate 22 according to a pattern controlled by pattern generator 38. Emissions from each sample point are collected by charged particle multiplier 40 to create an image that is displayed on video monitor 44 by way of video circuit 42. An operator viewing the image may adjust the voltages applied to various optical elements in column 16 to focus beam 18 and adjust beam 18 for various aberrations. Focusing optics in column 16 may comprise mechanisms known in the art for focusing or methods to be developed in the future.

Figure 4:
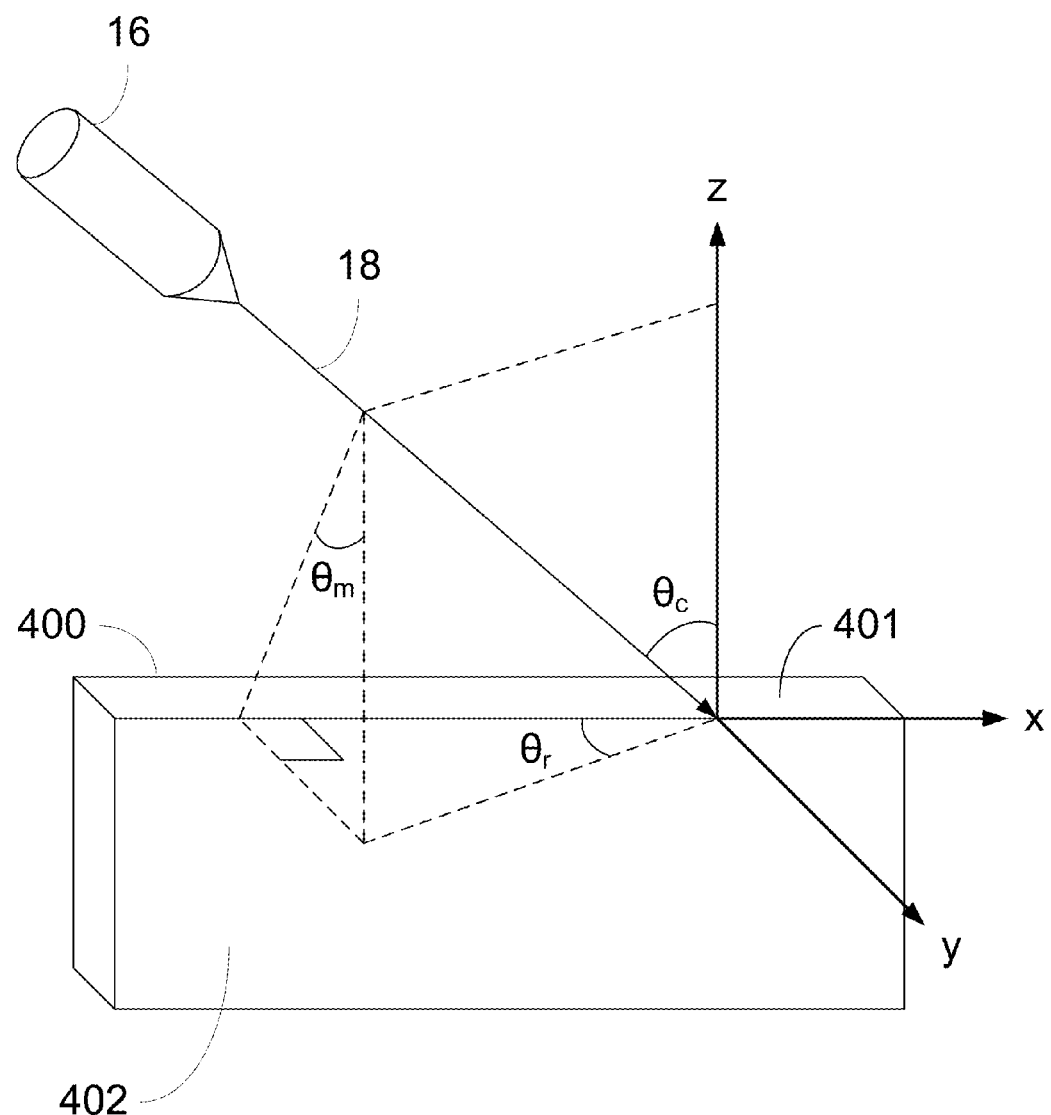
FIG. 4 shows an idealized three dimensional view of sample lamella 400 and ion beam 18 to demonstrate the various angles that are used to determine the orientation of ion beam 18 relative to lamella 400 in accordance with one or more embodiments of the present invention.

FIG. 4 shows an idealized three dimensional isometric view of sample lamella 400 and ion beam 18 to demonstrate the various angles that are used to determine the orientation of ion beam 18 relative to lamella 400 in accordance with one or more embodiments of the present invention. FIB column 16 directs ion beam 18 at a surface of lamella 400. The curtaining angle $\theta_c$ is the angle of ion beam 18 with respect to the z-axis. That is, curtaining angle $\theta_c$ is the angle between ion beam 18 and a normal to the top surface 401 of substrate 22. Put another way, curtaining angle $\theta_c$ is the angle of ion beam 18 from the z-axis, measured in the xz plane, when $\theta_r$ is equal to zero. In one embodiment of focused ion beam system 8 of FIG. 3, FIB column 16 is disposed in a fixed position within focused ion beam system 8 and curtaining angle $\theta_c$ cannot be varied. In an alternative embodiment, the tilt angle of FIB column 16 can be adjustable prior to milling lamella 400 from substrate 22, enabling focused ion beam system to mill different substrates at different curtaining angles. However, in this alternative embodiment, the position of FIB column 16 with respect to the top surface 401 of substrate 22 is not changed while milling lamella 400 from substrate 22 so that curtaining angle $\theta_c$ is constant throughout the milling process.

The rotation angle $\theta_r$ is the angle between of ion beam 18 and the x-axis projected into the xy plane.

The milling angle $\theta_m$ is the angle between ion beam 18 and the z-axis projected into the yz-plane. Milling angle $\theta_m$ can be determined from rotation angle $\theta_r$ and curtaining angle $\theta_c$ according to the following equation:

$$\theta_m = \tan^{-1}[\sin(\theta_r)\tan(\theta_c)],$$

where:
$\theta_m$=milling angle; component of FIB in plane of z-axis and lamella face normal
$\theta_c$=curtaining angle; mechanical angle between FIB and z-axis
$\theta_r$=rotation angle between FIB-z-axis plane and lamella plane Alternatively, the necessary sample stage rotation about the z-axis (i.e., rotation angle $\theta_r$) necessary to achieve the desired milling angle $\theta_m$ can be determined according to the following equation:

$$\theta_r = \sin^{-1}\left[\frac{\tan(\theta_m)}{\tan(\theta_c)}\right].$$

For example, if focused ion beam system 8 has FIB column 16 tilted 45 degrees with respect to the z-axis (i.e., curtaining angle $\theta_c$=45°), the relationship between necessary rotation angle $\theta_r$ and desired milling angle $\theta_m$ ends up being approximately linear for small milling angles $\theta_m$:

$$\tan\theta_c = 1$$

$$\theta_r = \sin^{-1}\left[\frac{\tan(\theta_m)}{\tan(\theta_c)}\right] = \sin^{-1}[\tan(\theta_m)]$$

for small $\theta_m$ $$\theta_r \approx \sin^{-1}[\sin(\theta_m)]$$

$$\theta_r \approx \theta_m$$

Figure 5:
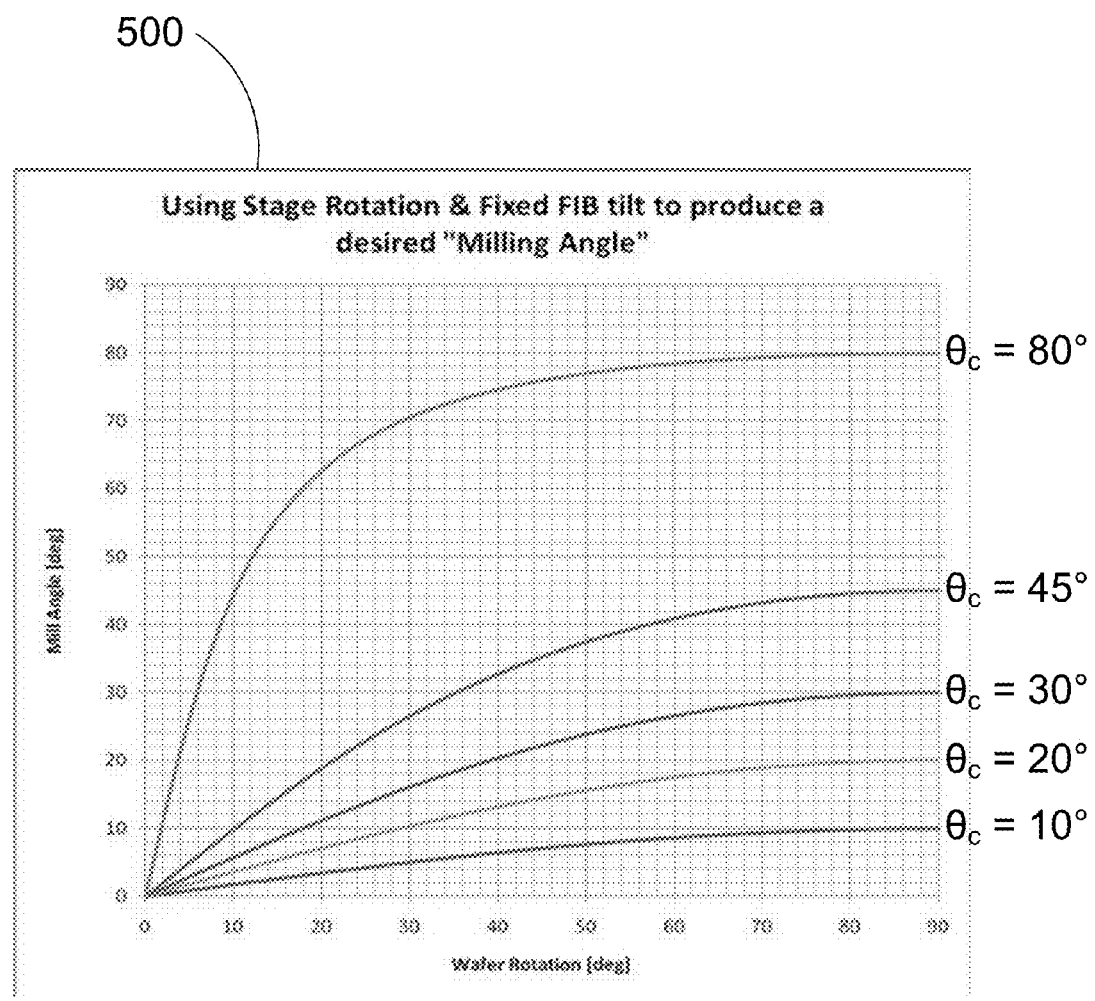
FIG. 5 shows a graph 500 illustrating milling angle $\theta_m$ as a function of rotation angle $\theta_r$ for various curtaining angles $\theta_c$.

To achieve a 6 degree milling angle $\theta_m$ in the example above, sample stage 24 is rotated 6 degrees, and the scanning pattern of ion beam 18 is rotated 6 degrees. Post-processing milling can then be performed without having to tilt sample stage 24 or FIB column 16 with respect to the other. If FIB column 16 is mounted with a curtaining angle $\theta_c$ that is much smaller than 45 degrees, the linear approximation no longer holds. FIG. 5 shows a graph 500 illustrating milling angle $\theta_m$ as a function of rotation angle $\theta_r$ for various curtaining angles $\theta_c$ ($\theta_c$=10, 20, 30, 45, and 80 degrees from the z-axis).

Figure 6:
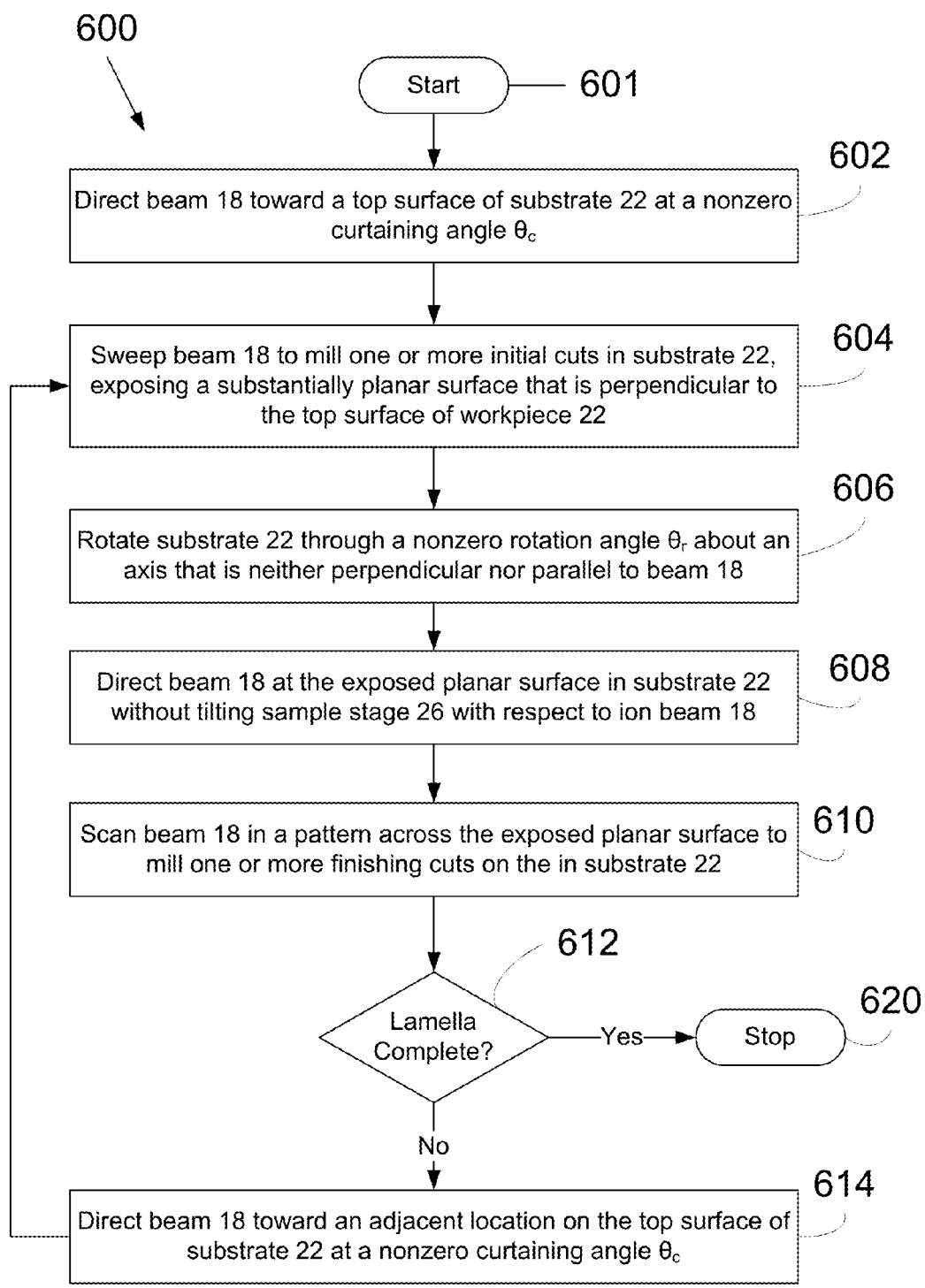
FIG. 6 shows a flowchart 600 showing a method of operating focused ion beam system 8 in accordance with one or more embodiments of the present invention.
Figure 7:
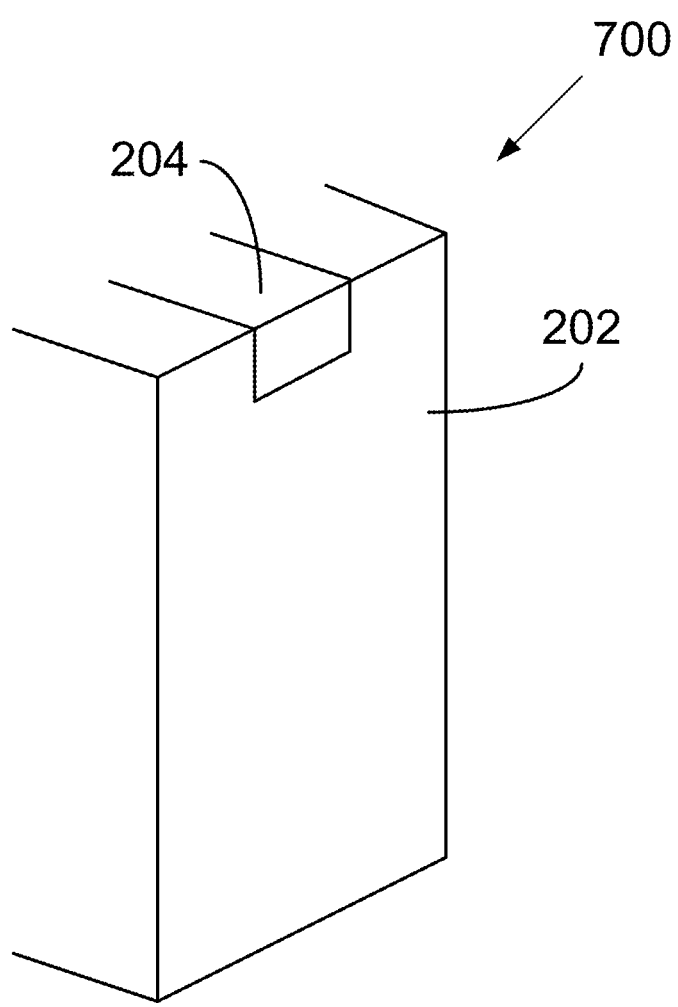
FIG. 7 shows a sample 700 exhibiting no curtaining effect.

FIG. 6 is a flowchart 600 showing a method of operating focused ion beam system 8 in accordance with one or more embodiments of the present invention. The method begins at initiator 601. At step 602, ion beam 18 is directed toward a horizontal top surface 401 of substrate 22 at a nonzero curtaining angle $\theta_c$. At step 604, ion beam 18 is swept in a plane to mill one or more initial cuts in substrate 22, exposing a substantially planar surface that is perpendicular to the top surface 401 of substrate 22. The initial cuts are "rough cuts" to remove bulk sample material from the substrate to expose the planar surface. By directing ion beam 18 at the substrate with a nonzero curtaining angle $\theta_c$, the shadows cast by materials in substrate 22 having higher mill rates are reduced compared to a vertically-oriented ion beam (i.e. an ion beam directed perpendicular to the top surface 401 of substrate 22). Reducing the shadows cast by materials in substrate 22 having higher mill rates reduces the undesirable surface variations due to the curtaining effect. FIG. 7 shows a sample 700 exhibiting no curtaining effect.

The planar surface may be tapered from top to bottom, due to the shape and energy distribution of ion beam 18. Also, during the initial cuts, material may be redeposited on or flow onto the planar surface. A first reason for finishing cuts is to remove any unwanted taper of the planar surface. A second purpose for finishing cuts is to remove a thin layer from a beam affected zone of the planar surface—this thin layer may comprise an amorphous layer, a redeposited layer, or a layer that flowed onto the planar surface. A third purpose for finishing cuts is to undercut the lamella in preparation for removal—this undercutting procedure comprises FIB milling at both the bottom and two side edges of the lamella. To make the finishing cuts, substrate 22 is rotated through a nonzero rotation angle $\theta_r$ about an axis that is neither perpendicular nor parallel to beam 18 (step 606). The rotation angle $\theta_r$ is determined according to the desired milling angle to be used for post-processing substrate 22. That is, instead of tilting sample stage 24 or FIB column 16 with respect to the other, sample stage 24 is rotated about an axis perpendicular to the top surface 401 of substrate 22 to achieve the desired milling angle. Milling angle $\theta_m$ can be determined from rotation angle $\theta_r$ and curtaining angle $\theta_c$ according to the following equation:

$$\theta_m = \tan^{-1}[\sin(\theta_r)\tan(\theta_c)],$$

where:

$\theta_m$=milling angle; component of FIB in plane of z-axis and lamella face normal $\theta_c$=curtaining angle; mechanical angle between FIB and z-axis $\theta_r$=rotation angle between FIB-z-axis plane and lamella plane After rotating substrate 22 through a nonzero rotation angle $\theta_r$, ion beam 18 is directed at the exposed planar surface in substrate 22 without tilting sample stage 24 with respect to ion beam 18 (step 608). Ion beam 18 is scanned in a pattern across the exposed planar surface to mill one or more finishing cuts in substrate 22 (step 610). After completion of the first cut in substrate 22, step 612 exits along the "No" branch, leading back to step 604 to initiate a second cut adjacent to the first cut. Completion of this second cut creates two cavities separated by a wall bounded by the two exposed planar surfaces. The wall separating the two cavities can be used as a lamella. After completion of the second cut, step 612 exits along the "Yes" branch to step 620, signifying completion of the lamella. One or more of the finishing cuts can include undercutting the wall at the base so that the wall can be removed.

Figure 8:
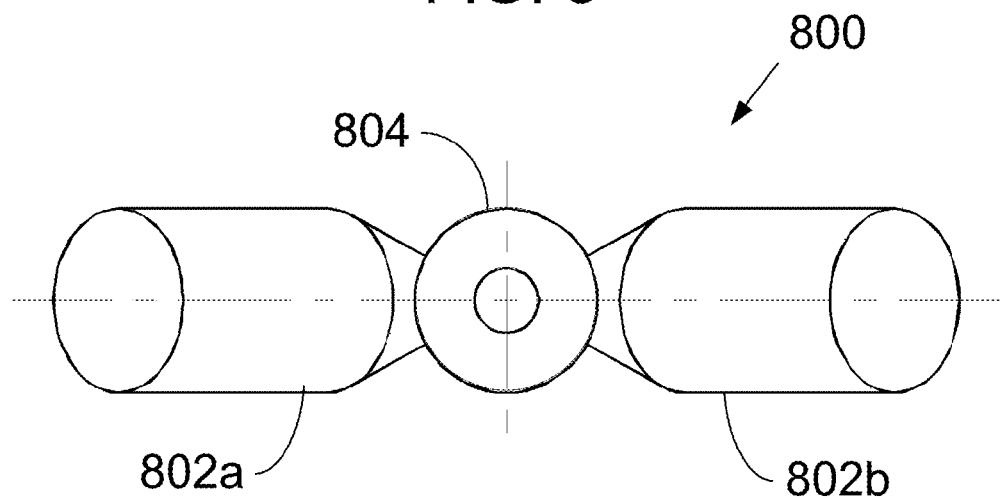
FIG. 8 shows a top schematic view of a three-column assembly 800 containing two FIB columns 802a and 802b, one on each side of a central SEM column 804.
Figure 9:
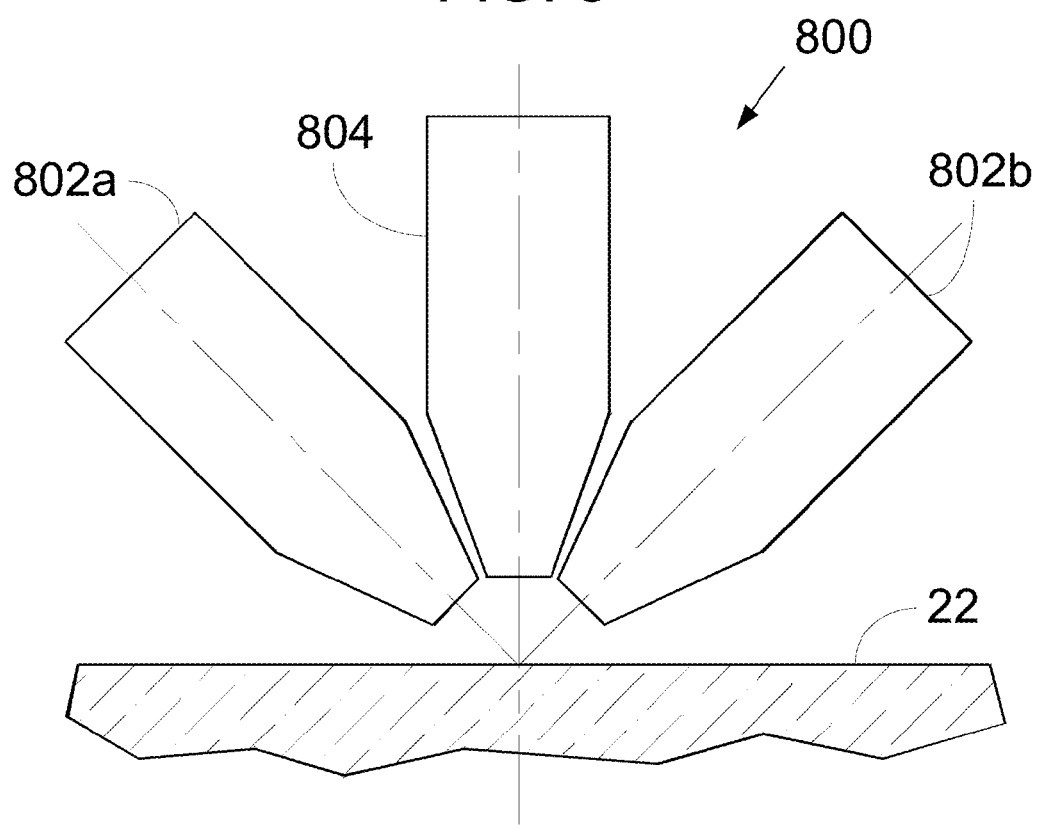
FIG. 9 shows a side schematic view of the three-column assembly 800 of FIG. 8 containing two FIB columns 802a and 802b, one on each side of a central SEM column 804.

To improve throughput and reduce processing time, embodiments of the present invention may include more than one FIB column and more than one electron beam column. FIG. 8 shows a top schematic view and FIG. 9 shows a side schematic view of a three-column assembly 800 containing two FIB columns 802a and 802b, one on each side of a central SEM column 804. For illustration, FIB columns 802a-802b are shown at 45 degree angles with respect to SEM column 804, but the exact angles may vary according to the size of the columns, the distance of the beams from substrate 22, and/or other factors. In the example shown here, the optical axes of the three columns 802a, 802b, and 804, converge to a single point on the surface of substrate 22 directly under the electron beam column. In other embodiments, it may be preferred to configure the three columns 802a, 802b and 804, so that the optical axes do not converge to a single point. In some embodiments, all the beams from columns 802a, 802b, and 804, may simultaneously be directed to the substrate 22. In other embodiments, only one or two of the beams from columns 802a, 802b, and 804, may be directed to the substrate 22 simultaneously. The above calculations for the determination of the curtaining angle $\theta_c$ apply for the case of multiple FIB columns as well as for the single FIB column illustrated in FIGS. 3 and 4. The arrangement of detectors for the columns may be one of the following:

1) Through-the-lens detectors within each column, all operating independently of each other. For SEM column 804, secondary and/or backscattered electrons could be collected to generate an imaging signal. For FIB columns 802a and 802b, secondary electrons or secondary ions could be collected to generate a supplemental imaging signal during milling and polishing. This signal could be used for endpoint detection.

2) One or more detectors located to the sides of the three columns (not shown), and capable of detecting secondary electrons, backscattered electrons and/or secondary ions in order to generate one or more imaging signals.

Figure 10:
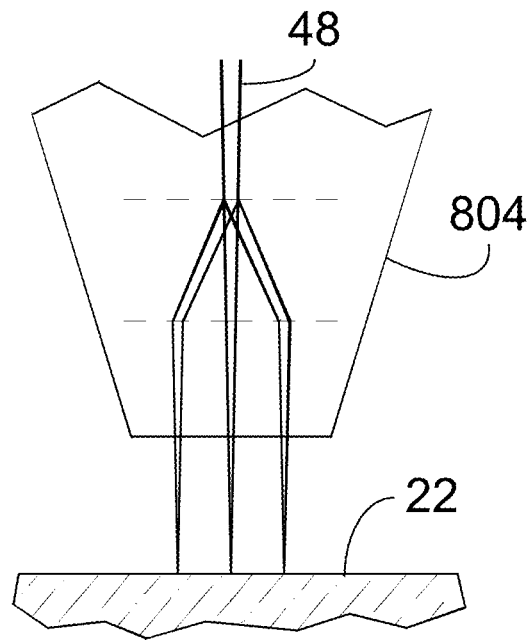
FIG. 10 is a side view illustrating an electron-beam imaging mode of a flat sample surface 22 prior to FIB milling.
Figure 11:
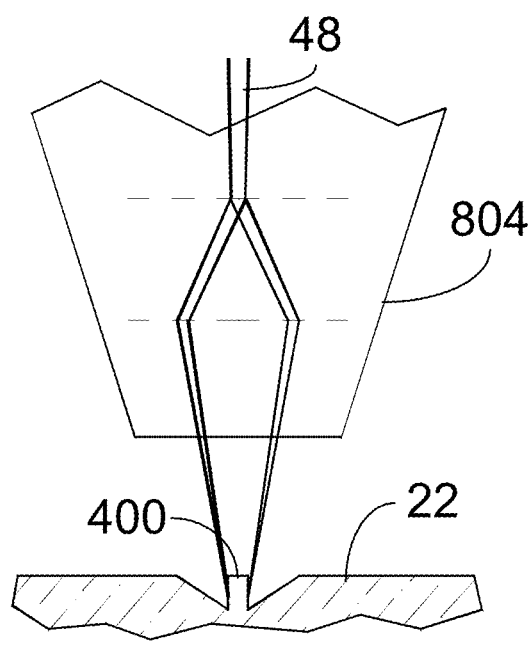
FIG. 11 is a side view illustrating an electron-beam imaging mode of the side walls of lamella 400.

FIG. 10 and FIG. 11 are side views illustrating two different electron-beam imaging modes employing SEM column 804. In FIG. 10, electron beam 48 is normally-incident to the surface of substrate 22—this mode would be useful during initial navigation around on substrate 22 to locate the specific features which are to be included in preparation of lamella 400. Electron beam 48 is scanned telecentrically to avoid positional errors induced by parallax which can occur with tilted beams. In FIG. 11, the double-deflection system within SEM column 804 is used to tilt electron beam 48 with respect to the two sides of lamella 400, enabling the sides to be imaged for endpoint detection (i.e., when the feature of interest is exposed, milling stops before the feature is milled away). In order to achieve adequate tilt angles (e.g., ±7 degrees to the substrate normal), a double-deflection system is employed which is optimized for large deflection angles and minimal deflection-induced aberrations.

Figure 12:
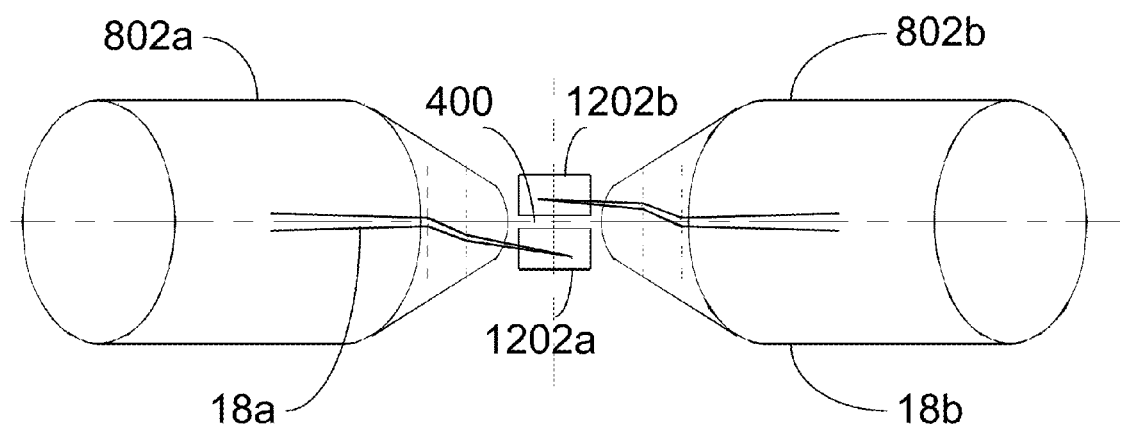
FIG. 12 shows focused ion beam columns 802a and 802b using ion beams 18a and 18b to simultaneously mill two cutouts 1202a and 1202b, one cutout on each side of lamella 400 to expose the vertical faces of lamella 400.
Figure 16:
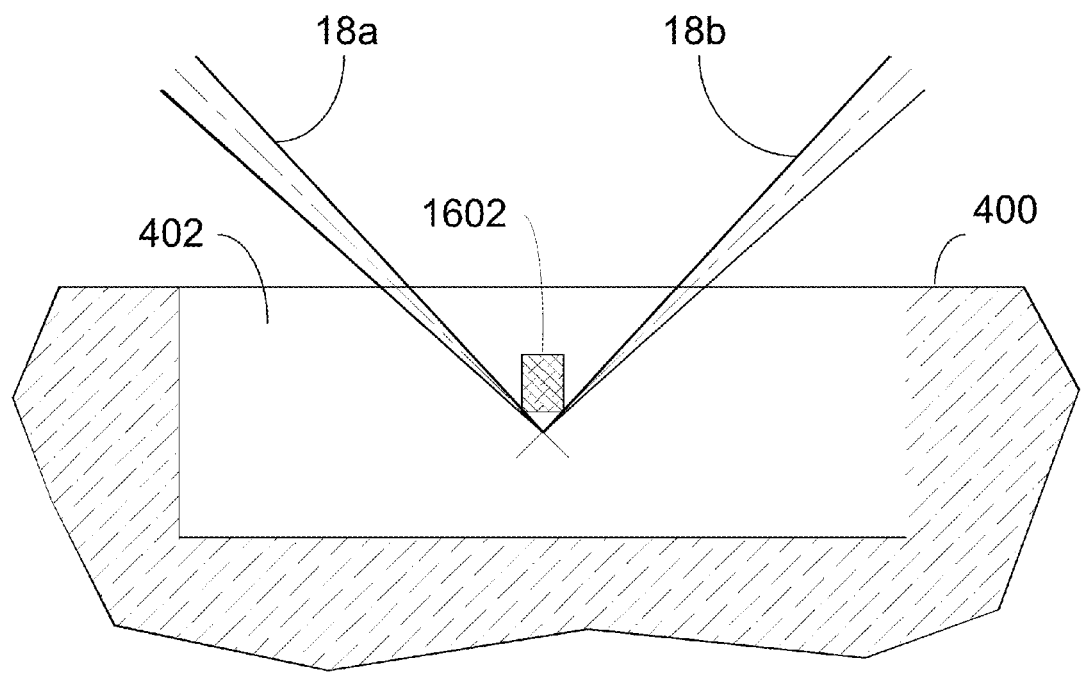
FIG. 16 illustrates a close-up side view from FIG. 15 of dual-FIB columns simultaneously polishing the same face 402 of lamella 400 to reduce curtaining.
Figure 17:
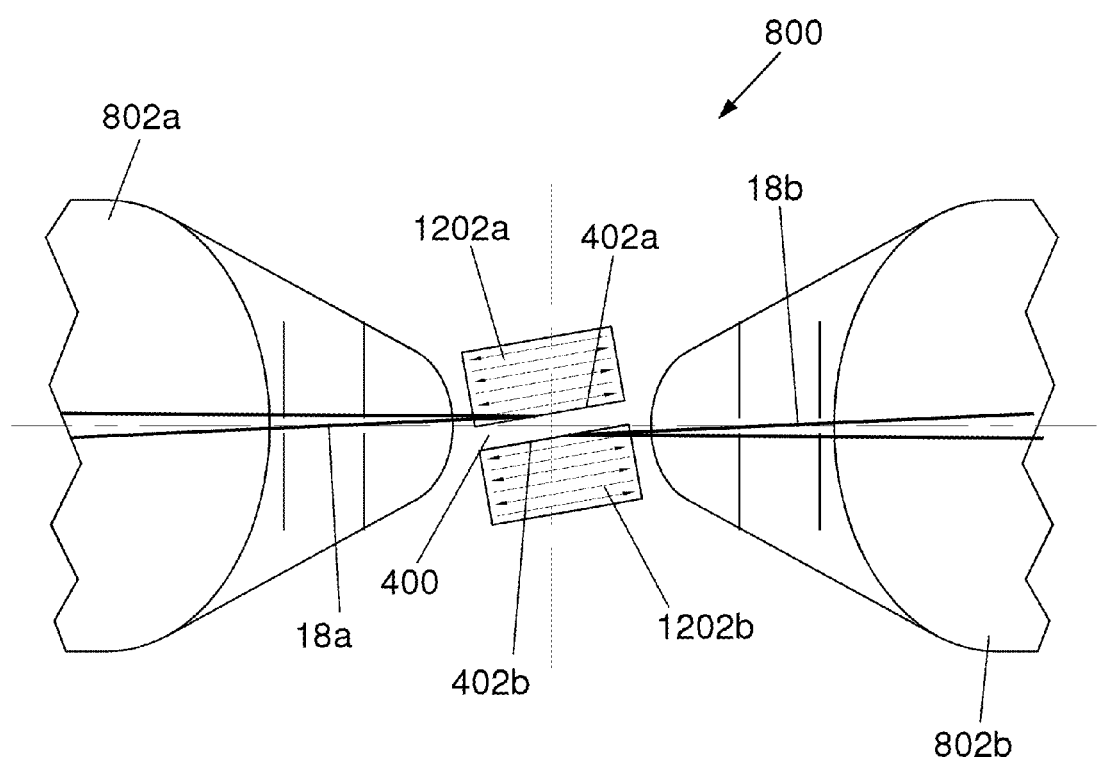
FIG. 17 illustrates the milling of finishing cuts in the lamella preparation process with a dual FIB system using stage rotation in accordance with a preferred embodiment of the present invention.

FIG. 12 shows focused ion beam columns 802a and 802b using ion beams 18a and 18b to simultaneously mill two cutouts 1202a and 1202b, one cutout on each side of lamella 400 to expose the vertical faces of lamella 400. SEM column 804 is not shown so that cutouts 1202a and 1202b can be seen. The FIB columns may have the same type of ion source (e.g., Ga) or may be configured with one column having a heavy ion source for rapid milling while the other column is configured with a lighter ion source for fine milling and polishing. It is also possible that each FIB column may have the same type of ion source, but different beam-defining apertures to enable one column to produce high ion fluxes for rapid (bulk) milling, while the other FIB column has smaller apertures to produce lower ion fluxes suitable for fine milling and polishing. In cases where the FIB columns differ, it may be necessary to compensate for the differential milling rates when curtaining is being removed, as illustrated in FIG. 16 and FIG. 17. Another alternative is to configure the FIB columns for multiple operating modes, wherein one mode produces a large beam with high currents, and another mode produces small beams with low currents—these alternative modes can be selectable by changes in lens voltages and/or by mechanical aperture motions.

Figure 13:
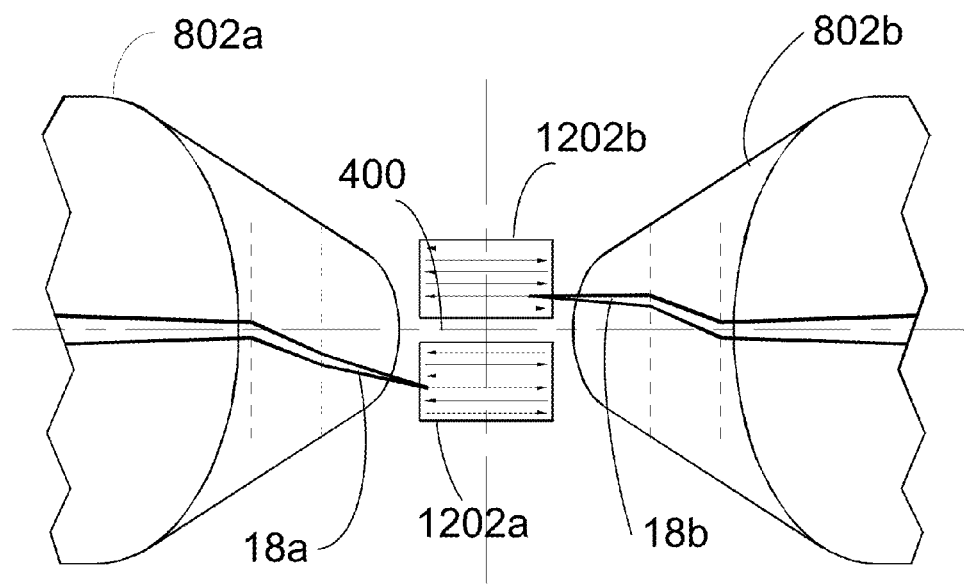
FIG. 13 is a close-up view of focused ion beam columns 802a and 802b and focused ion beams 18a and 18b from FIG. 12, showing how the two FIB columns may operate independently of each other.

FIG. 13 is a close-up view of focused ion beam columns 802a and 802b and focused ion beams 18a and 18b from FIG. 12, showing how the two FIBs may operate independently of each other, either milling on opposite sides of lamella 400 (shown) or both FIBs milling on the same side of lamella 400 (not shown). To mill cutouts 1202a and 1202b, the FIBs are scanned in modified raster patterns in which there are more scan lines near lamella 400 and fewer scan lines farther away from lamella 400. Scanning the FIBs in this modified raster pattern produces two triangular-shaped cutouts where the deepest side of each cutout creates one of the two faces of lamella 400. In this mode, the two FIBs will strike the top surface 401 of substrate 22 at roughly 45 degrees to the normal, which may increase the milling rates compared with normally-incident beams (this is a function of the particular ion species employed in the FIB columns). The substrate 22 rotation methodology described in FIGS. 3-5 for a single FIB column embodiment is equally applicable here for a dual FIB column embodiment, since both column tilt angles $\theta_c$ are fixed, while angles $\theta_m$, and $\theta_r$ will change simultaneously for columns 802a and 802b as the substrate 22 is rotated around an axis perpendicular to the surface of substrate 22. During this raster scanning process, the electron beam column may be periodically activated to produce an image of the cutouts in progress as an aid to end-pointing. The detectors within the FIB columns may also be used for real-time endpoint detection.

Figure 14:
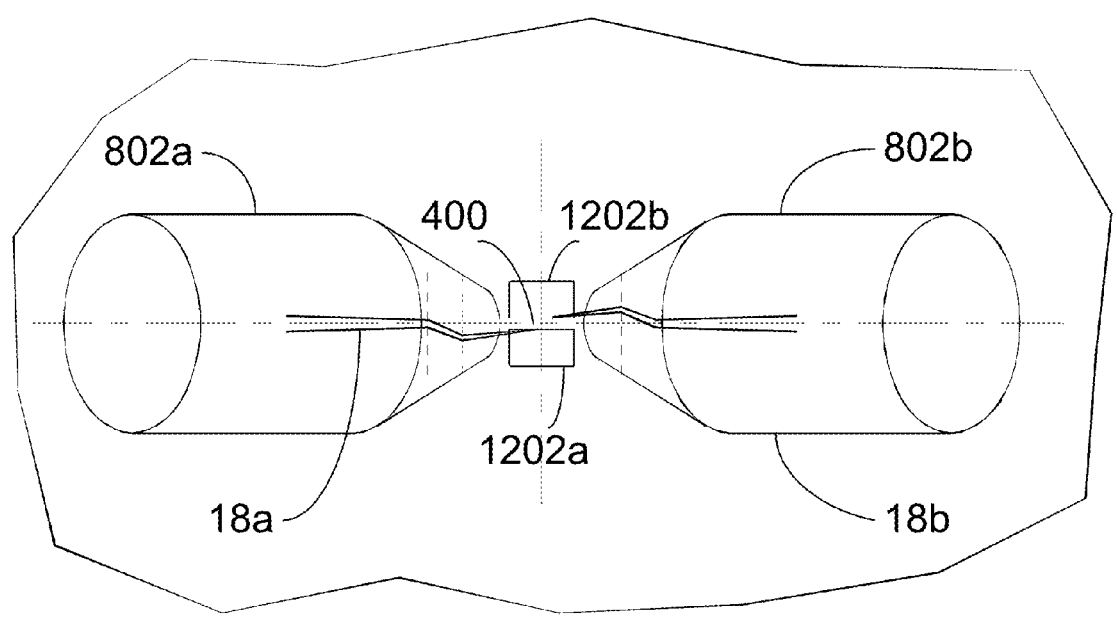
FIG. 14 illustrates a top view of the milling of finishing cuts in the lamella preparation process with a dual FIB system in accordance with an embodiment of the present invention.
Figure 15:
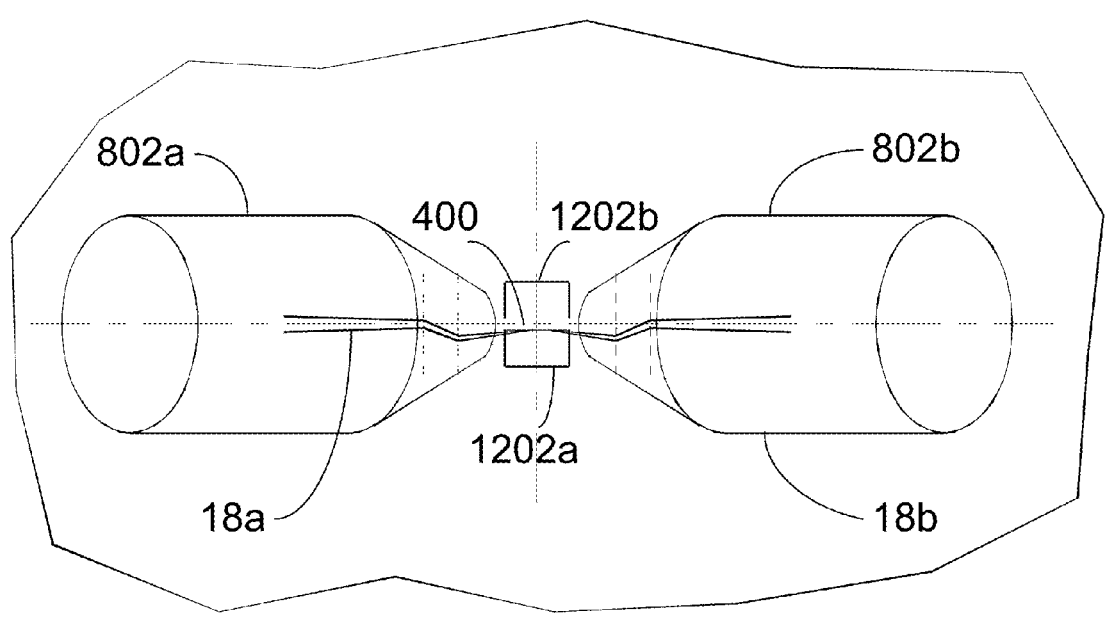
FIG. 15 illustrates a top view of dual-FIB columns simultaneously polishing the same face 402 of lamella 400 to reduce curtaining.

FIG. 14 and FIG. 15 illustrate the milling of finishing cuts in the lamella preparation process with a dual FIB system in accordance with an embodiment of the present invention. Cutouts 1202a and 1202b have been completed (see FIGS. 12-13) and now focused ion beams 18a and 18b are deflected against the substantially vertical faces of lamella 400 as shown. FIG. 14 illustrates the case where focused ion beams 18a and 18b are simultaneously milling on opposite sides of lamella 400. FIG. 15 illustrates the case where focused ion beams 18a and 18b are simultaneously milling on the same side of lamella 400. The double-deflectors within each FIB column are used to tilt the focused ion beams outwards so that they strike the lamella sides at a near grazing angle. For FIG. 14, substrate 22 may be rotated to direct the ion beams closer to the normal to the two lamella sides.

FIG. 16 is a close-up view of dual-FIBs 18a and 18b simultaneously polishing the same face 402 of lamella 400 to reduce curtaining. Protrusion 1602 is shown (e.g., a tungsten contact or via within the metal interconnect stack of the device—due to differential milling rates, these features may end up protruding due to slower milling than the other elements of the stack). For purposes of illustration, the two FIBs 18a and 18b have an enclosed angle of approximately 90 degrees in this example, although other enclosed angles may be used depending up on the application. The enclosed angle will generally be twice the angle between each of the FIB columns 802a and 802b and the SEM column 804 between them. If the SEM column 804 is mounted perpendicular to the substrate surface, a 90° enclosed angle corresponds to curtaining angles $\theta_c$=45° for both beams 18a and 18b. As can be seen in the figure, because the beams cross at a large angle, very little shadowing is possible beneath protrusion 1602, thereby reducing the curtaining under protrusion 1602.

FIG. 17 illustrates the milling of finishing cuts 1202a and 1202b in the lamella preparation process with a dual FIB system using stage rotation in accordance with a preferred embodiment of the present invention. Sample stage 24 and/or three column assembly 800 is rotated through non-zero rotation angle $\theta_r$, so that lamella 400 is rotated about an axis that is neither perpendicular nor parallel to focused ion beams 18a and 18b. After rotating sample stage 24 and/or three column assembly 800 through a nonzero rotation angle $\theta_r$, focused ion beams 18a and 18b are directed at the exposed planar surfaces 402a and 402b in lamella 400 without tilting sample stage 24 with respect to the ion beams. Ion beams 18a and 18b are then scanned in a pattern across the exposed planar surfaces 402a and 402b to mill one or more finishing cuts on lamella 400.

Figure 18:
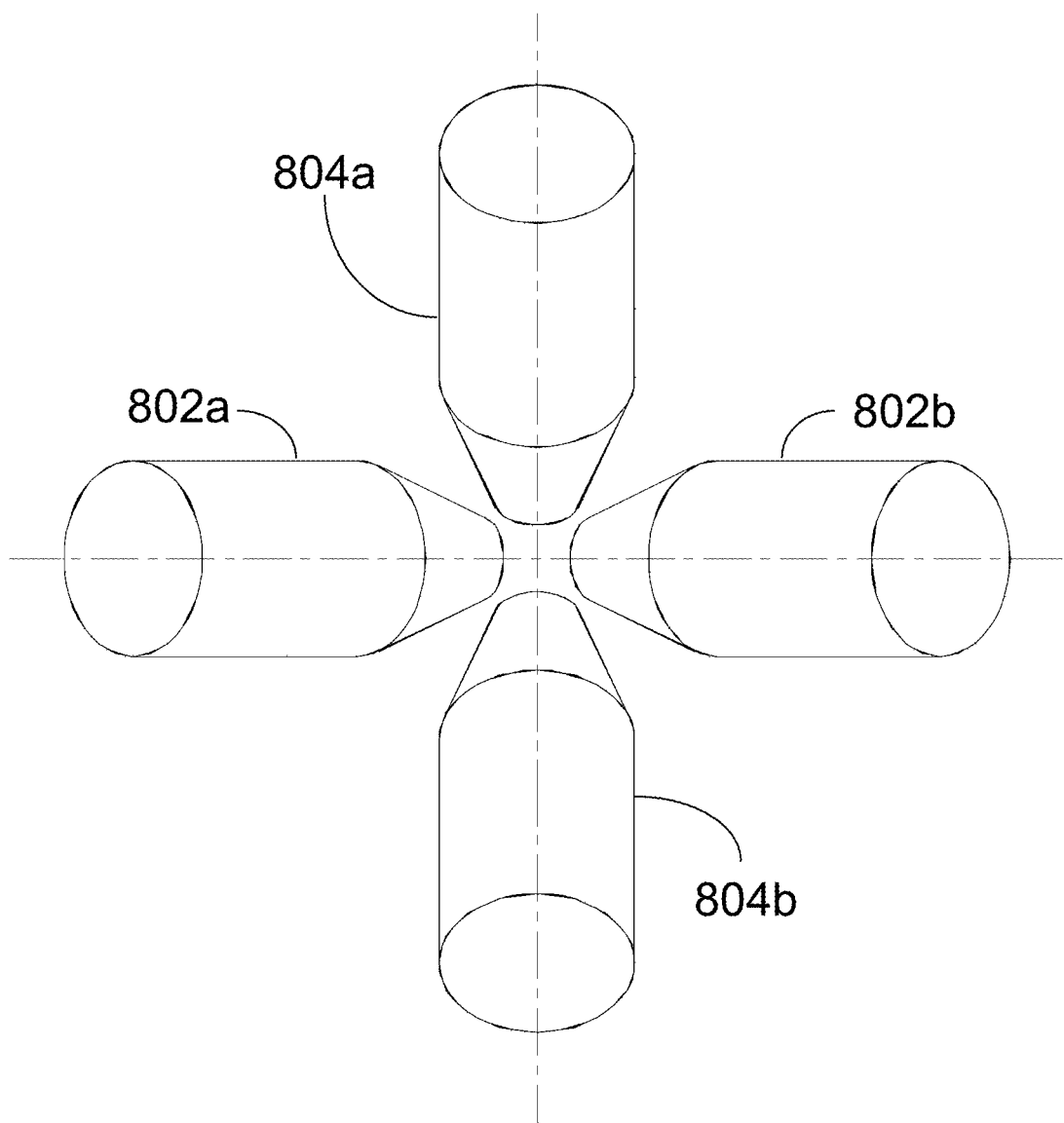
FIG. 18 shows an alternative embodiment of the present invention that includes two electron beam columns combined with two FIB columns.

FIGS. 8-17 have been described in relation to a three-column configuration comprising two focused ion beam columns 802a and 802b, one on each side of a single central electron beam column 804. Alternative column configurations are also possible within the scope of the present invention, including, but not limited to, the following:

1) Two Electron beam Columns and Two-FIB Columns—in this configuration, instead of a single electron beam column with its axis normal to the substrate surface, two electron beam columns 804a and 804b are combined with two FIB columns 802a and 802b, as illustrated in FIG. 18. The advantage of this configuration is that the two electron beams have a much better angle with respect to the sides of the lamella for imaging during milling, fine-milling and polishing. An obvious disadvantage is the additional cost for the second electron beam column and its supporting electronics. Some of this cost disadvantage may be mitigated through the use of mini-SEM and mini-FIB columns. In particular, an all-electrostatic SEM column, or mini-SEM column, may utilize less expensive electrostatic optics (lenses and voltage supplies) instead of the more expensive magnetic optics (magnetic coils and current supplies) employed in prior art SEM columns.

Figure 19:
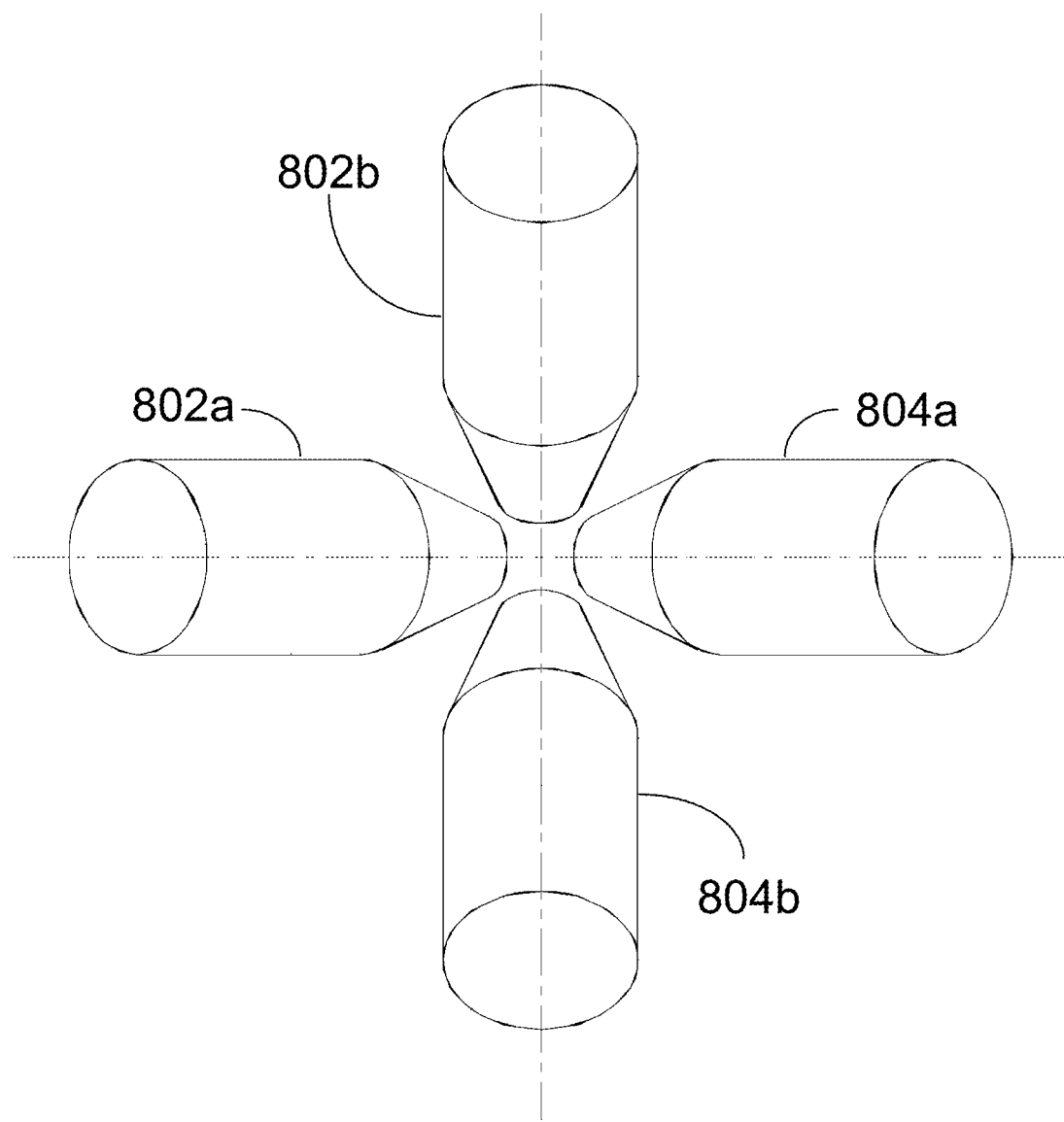
FIG. 19 shows another alternative embodiment of the present invention that includes two electron beam columns combined with two FIB columns.

2) Multiple Groups of Columns—in this configuration, two or more groups of columns are employed to further increase lamella-preparation throughput. For example, a system could comprise two groups of three columns, such as those shown in FIG. 8 and FIG. 9, which could be spaced apart along an axis perpendicular to the plane containing the three columns—this would enable the closest-packing of the columns, allowing for the smallest vacuum enclosure. Another embodiment could be two or more groups of four column assemblies (two electron beams and two FIBs, as shown in FIGS. 18 and 19).

3) One tilted Electron beam Column and Two FIB Columns—in this configuration (equivalent to FIG. 18 with one of the two Electron beam columns 804a and 804b removed), a single Electron beam (SEM) column would be mounted as shown in FIG. 18, accompanied by two FIB columns having an approximately 90 degrees enclosed angle between them as shown by the two FIB columns in FIG. 8. These two FIB columns produce focused ion beams with approximately a 90 degrees angle between them as illustrated in FIG. 16. In this concept, substrate 22 would be mounted on sample stage 24 with a rotation axis enabling the SEM column to image each side of the lamella during milling (the stage rotation axis would be perpendicular to the substrate). The two FIB columns can be identical, or can be configured such that one FIB column is optimized for higher current operation, probably at higher beam voltages, while the other FIB column is optimized for lower current operation, possibly at lower beam voltages.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of creating a sample lamella for observation by a transmission electron microscope, the method comprising forming a first substantially planar face of the sample lamella by:
    directing a first beam at a first surface of a substrate positioned on a sample stage to remove material from a first location in the substrate, the first beam being offset from a normal to the first surface by a first nonzero curtaining angle;
    sweeping the first beam in a plane that is perpendicular to the first surface to mill one or more first initial cuts in the substrate, the first initial cuts exposing a second surface that is tapered but substantially perpendicular to the first surface;
    determining a nonzero rotation angle according to the equation:

$$\theta_r = \sin^{-1}\left[\frac{\tan(\theta_m)}{\tan(\theta_c)}\right],$$

where $\theta_r$ is the nonzero rotation angle, $\theta_m$ is a desired milling angle, and $\theta_c$ is the nonzero curtaining angle;
    rotating the substrate without tilting the sample stage with respect to the first beam and through the nonzero rotation angle about an axis other than an axis that is normal to the first beam or parallel to the first beam;
    directing the first beam at the second surface to remove additional material from the substrate without changing the first nonzero curtaining angle; and
    scanning the first beam in a pattern across the second surface to mill one or more first finishing cuts in the substrate, the one or more first finishing cuts substantially removing the taper of the second surface,
    wherein rotating the substrate occurs after milling the one or more first initial cuts and before milling the one or more first finishing cuts.

2. The method of claim 1, further comprising forming a second substantially planar face of the sample lamella by:
    directing a second beam at the first surface of the substrate to remove material from a second location in the substrate, the second beam being offset from a normal to the first surface by a second nonzero curtaining angle, the second location in the substrate disposed sufficiently proximal to the first location in the substrate to form a lamella of a desired thickness;
    sweeping the second beam in a plane that is perpendicular to the first surface to mill one or more second initial cuts in the substrate, the second initial cuts exposing a third surface that is tapered but substantially perpendicular to the first surface and substantially parallel to the second surface;
    rotating the substrate without tilting the sample stage with respect to the second beam and through a nonzero rotation angle about an axis other than an axis that is normal to the second beam or parallel to the second beam;
    directing the second beam at the third surface to remove additional material from the substrate without changing the second nonzero curtaining angle; and
    scanning the second beam in a pattern across the third surface to mill one or more second finishing cuts in the substrate, the one or more second finishing cuts substantially removing the taper of the third surface,
    wherein rotating the substrate without tilting the sample stage with respect to the second beam and through the nonzero rotation angle about the axis other than the axis that is normal to the second beam or parallel to the second beam occurs after milling the one or more second initial cuts and before the one or more second finishing cuts.

3. The method of claim 1, further comprising rotating the substrate through a nonzero rotation angle about an axis perpendicular to the first surface.

4. The method of claim 1, in which the first beam is selected from a group comprising: a focused ion beam, an electron beam, a laser beam, and a water jet from a water jet cutter.

5. The method of claim 2, in which the second beam is selected from a group comprising: a focused ion beam, an electron beam, a laser beam, and a water jet from a water jet cutter.

6. The method of claim 1, further comprising imaging the substrate with a scanning electron microscope during milling.

7. The method of claim 1, in which the first nonzero curtaining angle is the angle between the beam and a normal to the first surface of the substrate.

8. The method of claim 1, in which the nonzero rotation angle is the angle between a plane including the beam and the axis about which the substrate is rotated and a plane including the second surface of the substrate.

9. The method of claim 2, in which the directing of said first beam and the directing of said second beam occurs time-sequentially, and wherein said first beam and said second beam are the same beam.

10. The method of claim 2, in which the directing of said first beam and the directing of said second beam occurs generally concurrently, and wherein said first beam and said second beam are different beams.

11. The method of claim 1, in which the one or more first finishing cuts removes material that is redeposited on and/or flows onto the second surface during and/or after milling the one or more first initial cuts.

12. The method of claim 1, in which the one or more first finishing cuts remove material on the second surface that has been made amorphous during milling of the one or more first initial cuts.

13. The method of claim 2, in which the one or more first finishing cuts and the one or more second finishing cuts substantially remove variations in thickness between the top and the bottom of the lamella.

14. The method of claim 2, in which the one or more first finishing cuts and the one or more second finishing cuts separate the lamella from the substrate.

15. The method of claim 2, further comprising directing a first beam and second beam at the substrate to increase throughput, the first beam removing material from the first location in the substrate, and the second beam removing material from the second location in the substrate.

16. The method of claim 2, in which the method is performed automatically without manual intervention from an operator.

17. The method of claim 15, further comprising directing the first beam at the second surface to remove additional material from the substrate, and directing the second beam at the third surface to remove additional material from the substrate.

18. A method for creating a substantially planar face in a substrate comprising:
  directing a first beam at a first surface of a substrate to remove material from a first location in the substrate, the first beam being offset from a normal to the first surface by a first nonzero curtaining angle, the substrate being positioned on a sample stage that can rotate about no more than one axis, the one axis being an axis other than an axis that is normal to the first beam or parallel to the first beam;
  sweeping the first beam in a plane that is perpendicular to the first surface to mill one or more initial cuts in the substrate, the initial cuts exposing a second surface that is substantially perpendicular to the first surface;
  determining a nonzero rotation angle according to the equation:

$$\theta_r = \sin^{-1}\left[\frac{\tan(\theta_m)}{\tan(\theta_c)}\right],$$

where $\theta_r$ is the nonzero rotation angle, $\theta_m$ is a desired milling angle, and $\theta_c$ is the nonzero curtaining angle;
  rotating the substrate through the nonzero rotation angle about the one axis;
  directing the first beam at the second surface to remove additional material from the substrate without changing the first nonzero curtaining angle; and
  scanning the first beam in a pattern across the second surface to mill one or more finishing cuts in the substrate.

* * * * *